United States Patent
Kim et al.

(10) Patent No.: US 8,673,371 B2
(45) Date of Patent: Mar. 18, 2014

(54) COMPOSITION FOR TREATING VITILIGO OR CANITIES COMPRISING EXTRACT FROM SOPHORA JAPONICA AS ACTIVE INGREDIENT

(75) Inventors: Young Chul Kim, Daegu (KR); Chul Ho Kang, Daejeon (KR); Eun Ye Park, Daegu (KR); Sang Nam Kim, Gyeongbuk (KR)

(73) Assignee: Keimyung University Industry Academic Cooperation Foundation, Daegu (KR)

( * ) Notice: Subject to any disclaimer, the term of this patent is extended or adjusted under 35 U.S.C. 154(b) by 124 days.

(21) Appl. No.: 13/277,605

(22) Filed: Oct. 20, 2011

(65) Prior Publication Data

US 2012/0156315 A1    Jun. 21, 2012

(30) Foreign Application Priority Data

Dec. 17, 2010 (KR) .................. 10-2010-0129621

(51) Int. Cl.
*A61K 36/00* (2006.01)
(52) U.S. Cl.
USPC ........................................... 424/725
(58) Field of Classification Search
None
See application file for complete search history.

(56) References Cited

U.S. PATENT DOCUMENTS

| 5,872,254 | A  | * | 2/1999 | Kim et al. .................. 546/242 |
| 2009/0192124 | A1 | * | 7/2009 | Pelletier et al. ............. 514/162 |
| 2010/0099698 | A1 | * | 4/2010 | Park et al. .................. 514/287 |
| 2012/0121743 | A1 | * | 5/2012 | Garnier et al. ............... 424/777 |
| 2012/0237624 | A1 | * | 9/2012 | Msika et al. ................. 424/757 |

FOREIGN PATENT DOCUMENTS

| CN | 1813875 | * | 6/2006 |
| CN | 101040834 | * | 9/2007 |
| JP | 2001-131025 | * | 5/2001 |
| JP | 2002-060318 | * | 2/2002 |
| KR | 2004091178 | * | 10/2004 |

OTHER PUBLICATIONS

Kim et al., "Tyrosinase Inhibitors from Natural and Synthetic Sources: Structure, Inhibition Mechanism and Perspective for the Future," Cell Mol. Life Sci. 62:1707-1723, 2005 (abstract).
Lo et al., "Active Constituents from Sophora Japonica Exhibiting Cellular Tyrosinase Inhibition in Human Epidermal Melanocytes," J. Ethnopharmacol. 124:625-629, 2009 (abstract).
Wang et al., "Cosmetic Applications of Selected Traditional Chinese Herbal Medicines," J. Ethnopharmacol. 106:353-359, 2006.

* cited by examiner

*Primary Examiner* — Chris R Tate
(74) *Attorney, Agent, or Firm* — Clark & Elbing LLP

(57) ABSTRACT

Disclosed is a composition for treating or preventing vitiligo or canities comprising *Sophora japonica* extract as an active ingredient. The *Sophora japonica* extract enhances melanin synthesis by increasing the activity of tyrosinase which is critical in intracellular melanin synthesis and promoting the expression of tyrosinase and TRP-2 mRNA. Furthermore, since the *Sophora japonica* extract is a natural substance with little cytotoxicity, it may be developed into a therapeutic agent for vitiligo and canities caused by depigmentation in skin and hair.

4 Claims, 11 Drawing Sheets

COMPOSITION FOR TREATING VITILIGO OR CANITIES COMPRISING EXTRACT FROM SOPHORA JAPONICA AS ACTIVE INGREDIENT

CROSS-REFERENCE TO RELATED APPLICATIONS

This application claims priority under 35 U.S.C. §119 to Korean Patent Application No. 10-2010-0129621, filed on Dec. 17, 2010, in the Korean Intellectual Property Office, the disclosure of which is incorporated herein by reference in its entirety.

TECHNICAL FIELD

The present disclosure relates to a composition for treating vitiligo or canities containing *Sophora japonica* extract as an active ingredient.

BACKGROUND

In patients with vitiligo, the white patches greatly affect their quality of life (Ongenae et al. 2006). Vitiligo may seem a minor disorder on first sight, but, people with severe depigmentation may have troubles in dating (Papadopoulos et al. 1999) or self-esteem or social activities psychologically (Kent et al. 1996). Therefore, modification of skin pigmentation using whitening agents and coloring agents has gained a lot of attention in the field of pharmacology and cosmeceuticals (Michaela and Vincent 2008).

Melanin is secreted by melanocytes found in the basal layer of the dermis (Kim and Uyama 2005). Upon biosynthesis by the melanocytes differentiating in the neural crest, melanin is transferred to the epidermis by keratinocytes (Yaar et al. 2006). The melanocyte has a specialized organelle called melanosome, which regulates melanin production and contains various enzymes (Tiedtke et al. 2004). Melanin plays important roles of protecting the skin from harmful effects by absorbing UV, removing reactive oxygen species and scavenging toxic drugs and chemicals (Yaar et al. 2006).

Melanin synthesis is catalyzed by tyrosinase-related protein 1 (TRP1) and tyrosinase-related protein 2 (TRP2 or DCT) (Huang et al. 2008). In the skin exposed to UV radiation, melanin synthesis is initiated by the enzyme tyrosinase (Parvez et al. 2006). Tyrosinase, which is known as an important enzyme that catalyzes melanin synthesis in the melanocytes (Sturm et al. 2000), plays an important role in oxidizing tyrosine to DOPA and DOPA to dopaquinone (Tripathi et al. 1992). Dopaquinone is spontaneously converted to dopachrome. TRP2 (DCT) catalyzes the conversion of dopachrome to DHICA, and TRP1 catalyzes the oxidation of DHICA to indole-5,6-quinone-2-carboxylic acid (Kim and Uyama 2005).

Vitiligo is a depigmentation condition characterized by localized depigmented patches caused by loss of melanin in the epidermis or functional inability of melanocytes (Helen et al. 2007). In order to explain the dysfunction of melanocytes in the epidermis, the autoimmune mechanism, the autocytotoxic mechanism and the hypothesis that abnormal melanocytes nearby keratinocytes lose their function are presented (Ongenae 2003; Moretti 2002). Other causes of vitiligo include stress, infection, genetic factors, melatonin receptors, and migration and proliferation of damaged melanocytes (Helen et al. 2007). 3-Isobutyl-1-methylxanthine (IBMX), which is a strong stimulant of melanin synthesis (David 2001), increases cAMP content in cells by inhibiting cAMP phosphodiesterase (Im et al. 1998), and dibutyryl cAMP increases tyrosinase activity and mRNA expression (Hoganson et al 1989). MITF is a master regulator of melanocyte development and melanin synthesis (Levy et al. 2006) and regulates transcription of the major pigmentation enzymes, tyrosinase, TRP-1 and TRP-2 (Koo et al. 2008).

At present, topical application of corticosteroid, calcineurin inhibitor, vitamin D derivatives, phototherapy (UVA, narrowband UVB, photochemical therapy), surgery, and a combination of topical treatment and phototherapy are tried for the treatment of vitiligo (Maxine et al. 2008). It is reported that the patients who refuse the photochemical therapy have increased incidence of non-melanoma and melanoma skin cancer (Rajatanavin et al. 2003). Accordingly, efforts are made to find natural substances for development of new skin care medicines and the use of natural substances in skin care cosmetics is becoming more important (Kiken et al. 2002).

Canities (hair graying) is caused by decreased tyrosinase activity of hair bulbar melanocytes due to toxic oxidation of the melanocytes and defective migration of the melanocytes from the reservoir in the upper outer root sheath to the pigment-permitting microenvironment close to the dermal papilla (Neste and Tobin 2004; Tobin et al. 2001). Canities is one of the typical signs of human aging and the maintenance of hair color depends on the consistent presence of melanocytes and retention of their function (Kerscher et al. 2007; Lin and Fisher 2007; Sarin et al. 2007). Melanocyte stem cells (MSCs) were found in the hair follicle. Unlike epithelial melanocytes, hair follicle melanocytes are produced in the early stage of each hair cycle and undergo apoptosis at the end thereof. When the cycle repeats 7-15 times over 45 years or longer, the hair follicle cannot produce melanin any more. Since the hair follows the regular cycling/re-pigmentation processes during lifetime, the gradual loss of hair color with aging in animals including human and mouse suggests that the canities may be caused by the damaged self-maintenance ability of the MSCs.

Plant compounds known to have useful activities are utilized in the manufacture of cosmetics (Huang et al. 2008). The flower and flower bud of *Sophora japonica* are well known as traditional medicinal herb in China (Loa et al. 2009) and have antitumor, antisterilic and anticancer activities (Ma 2006; Wang 2001). The ingredients of *Sophora japonica* include flavonol triglucoside, isoflavonol, cumaronchromone, saponin, triterpene glucoside, phospholipid, alkaloid, amino acid, polysaccharide and fatty acid (Grupp et al. 2001). *Sophora japonica* extract is usually used to treat hemorrhage-related disorders such as bloody excrement, rectal hemorrhage, uterine hemorrhage and diarrhea (Zhao 2004).

Throughout the specification, a number of publications and patent documents are referred to and cited. The disclosure of the cited publications and patent documents is incorporated herein by reference in its entirety to more clearly describe the state of the related art and the present disclosure.

SUMMARY

The inventors of the present disclosure have studied to develop therapeutic substances for depigmentation diseases such as vitiligo and canities from natural products. As a result, they have experimentally demonstrated that the extract obtained from *Sophora japonica* enhances melanin synthesis by increasing the activity of tyrosinase, which is critical in melanin synthesis, and promoting the expression of tyrosinase and TRP-2 mRNA.

The present disclosure is directed to providing a composition for treating, preventing or improving vitiligo or canities comprising *Sophora japonica* extract as an active ingredient.

Other features and aspects will be apparent from the following detailed description, the drawings, and the claims.

BRIEF DESCRIPTION OF THE DRAWINGS

The above and other objects, features and advantages of the present disclosure will become apparent from the following description of certain exemplary embodiments given in conjunction with the accompanying drawings, in which.

DETAILED DESCRIPTION OF EMBODIMENTS

Figure 1:
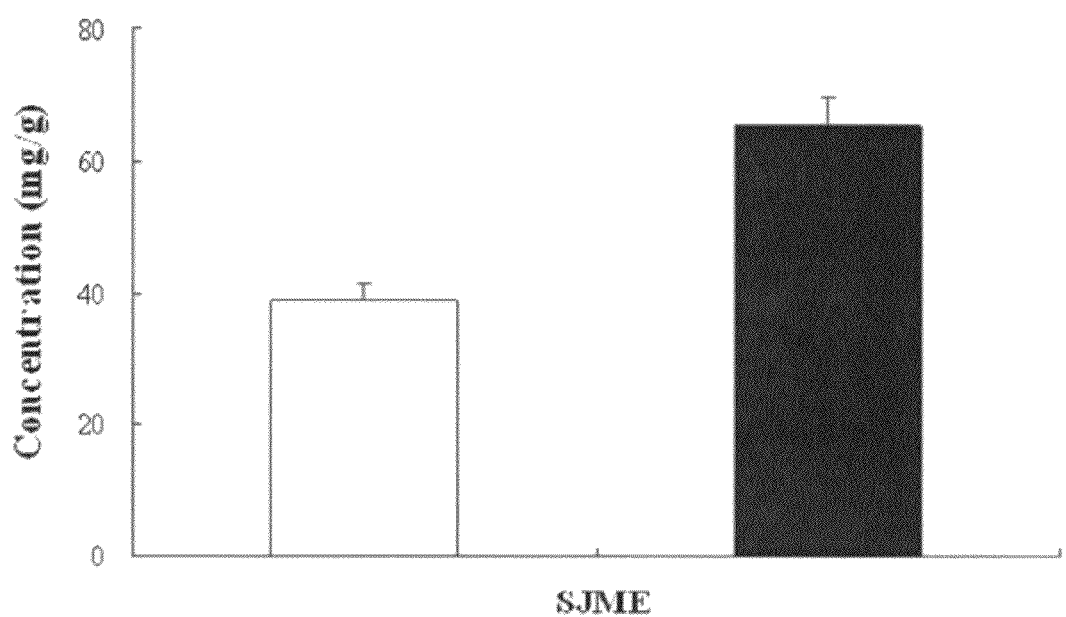
FIG. 1 shows a result of measuring total polyphenol and flavonoid contents of *Sophora japonica* methanol extract (Values are mean±SD of 3 measurements. SJME: *Sophora japonica* methanol extract, □: total polyphenol, ■: total flavonoid)

The advantages, features and aspects of the present disclosure will become apparent from the following description of the embodiments with reference to the accompanying drawings, which is set forth hereinafter. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. The terminology used herein is for the purpose of describing particular embodiments only and is not intended to be limiting of the example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawings.

In a general aspect, the present disclosure provides a pharmaceutical composition for treating or preventing vitiligo or canities comprising *Sophora japonica* extract as an active ingredient.

In another general aspect, the present disclosure provides a cosmetic composition for improving vitiligo or canities comprising *Sophora japonica* extract as an active ingredient.

In another general aspect, the present disclosure provides a method for treating vitiligo or canities, which comprises topically applying a topical composition comprising *Sophora japonica* extract on one or more areas of the skin of a person who is suffering from vitiligo or canities, thereby achieving reduction of vitiligo or canities.

The *Sophora japonica* extract may be isolated according to a method commonly employed in the art to obtain extracts from natural products, i.e. under common temperature and pressure conditions using a commonly used solvent. The *Sophora japonica* extract refers to an extract obtained from any part of *Sophora japonica*, including leaves, trunk, root and fruit, without being limited to specific parts.

A solvent commonly used for extraction may be used as an extraction solvent for extracting the *Sophora japonica* extract. Also, two or more different solvents may be used sequentially for the extraction. Specifically, the extraction solvent of the present disclosure may be a solvent selected from the group consisting of water, absolute or aqueous lower alcohol containing 1-4 carbons (e.g., methanol, ethanol, propanol or butanol), acetone, ethyl acetate, butyl acetate, dichloromethane ($CH_2Cl_2$), chloroform, hexane and 1,3-butylene glycol. More specifically, methanol, n-hexane, dichloromethane, ethyl acetate or water may be used. Most specifically, methanol may be used.

In an exemplary embodiment of the present disclosure, the *Sophora japonica* extract is included at a concentration of 0.001-30 wt % based on the total weight of the composition.

"Vitiligo" which is a treatment target of the present disclosure is a depigmentation condition characterized by localized depigmented patches caused by loss of melanin in the epidermis or functional inability of melanocytes. And, "canities" also known as "hair graying" refers to a condition wherein the tone of individual hairs become weak gradually, leading to coexistence of hairs of varying color tones from normal to white. The cause of canities is known to be caused by decreased tyrosinase activity of hair bulbar melanocytes due to toxic oxidation of the melanocytes.

As demonstrated in the following examples, the *Sophora japonica* extract promotes melanin production by greatly increasing the activity of tyrosinase, which is critical in melanin synthesis in cells. Accordingly, the *Sophora japonica* extract can be usefully used to treat, prevent and improve vitiligo and canities.

The pharmaceutical composition of the present disclosure may comprise a pharmaceutically acceptable carrier in addition to the *Sophora japonica* extract as the active ingredient. The carrier may be commonly used one, for example, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in *Remington's Pharmaceutical Sciences* (19th ed., 1995).

An appropriate dosage of the pharmaceutical composition of the present disclosure may be determined variously depending on such factors as preparation method, administration method, age, body weight and sex of the patient, pathological condition, diet, administration time, administration route, excretion rate or response sensitivity. Specifically, an oral dosage of the pharmaceutical composition of the present disclosure for an adult may be 0.0001-100 mg/kg (body weight) per day.

The pharmaceutical composition of the present disclosure may be administered orally or parenterally. When administered parenterally, it may be administered topically, intravenously, subcutaneously, intramuscularly, intraabdominally or transdermally. Specifically, considering that the pharmaceutical composition of the present disclosure is used for treatment or prevention of vitiligo or canities caused by melanin deficiency, the present disclosure composition may be administered by topically applying to the skin.

The concentration of the active ingredient included in the composition of the present disclosure may be determined considering purpose of treatment, patient's condition, required period, or the like, and is not particularly limited.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, emulsion, extract, powder, granule, tablet or capsule, and may further include a dispersant or stabilizer.

In an exemplary embodiment of the present disclosure, the pharmaceutical composition of the present disclosure is formulated for application to skin. The formulation form is not particularly limited and may be, for example, powder, gel, ointment, cream, lotion, liquid or aerosol.

The present disclosure also provides a cosmetic composition for improving vitiligo or canities comprising the *Sophora japonica* extract as an active ingredient.

The cosmetic composition of the present disclosure may be prepared into any formulation common in the art. For example, it may be formulated into solution, suspension, emulsion, paste, gel, cream, lotion, powder, soap, surfactant-containing cleanser, oil, powder foundation, emulsion foundation, wax foundation, spray, etc., but without being limited thereto. More specifically, it may be formulated into emollient lotion, nourishing lotion, nourishing cream, massage cream, essence, eye cream, cleansing cream, cleansing foam, cleansing water, pack, spray or powder.

When the formulation of the present disclosure is in the form of paste, cream, lotion or gel, animal oil, plant oil, wax, paraffin, starch, tragacanth, cellulose derivatives, polyethylene glycol, silicone, bentonite, silica, talc, zinc oxide, etc. may be used as a carrier.

When the formulation of the present disclosure is in the form of powder or spray, lactose, talc, silica, aluminum hydroxide, calcium silicate or polyamide powder may be used as a carrier. Especially, when it is in the form of spray, the formulation may further comprise a propellant such as chlorofluorohydrocarbon, propane/butane or dimethyl ether.

When the formulation of the present disclosure is in the form of solution or emulsion, a solvent, solubilizer or emulsifier may be used as a carrier. For example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol or fatty acid ester of sorbitan may be used.

When the formulation of the present disclosure is in the form of suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier.

When the formulation of the present disclosure is in the form of surfactant-containing cleanser, aliphatic alcohol sulfate, aliphatic alcohol ether sulfate, sulfosuccinic monoester, isethionate, imidazolinium derivatives, methyl taurate, sarcosinate, fatty acid amide ether sulfate, alkyl amidobetaine, aliphatic alcohol, fatty acid glyceride, fatty acid diethanolamide, vegetable oil, lanolin derivatives, ethoxylated glycerol fatty acid ester, etc. may be used as a carrier.

The cosmetic composition of the present disclosure may further comprise, in addition to the active ingredient as well as the carrier, other components commonly included in the cosmetic composition. For example, common adjuvants such as antioxidant, stabilizer, solubilizer, vitamin, pigment and fragrance may be included.

EXAMPLES

The examples and experiments will now be described. The following examples and experiments are for illustrative purposes only and not intended to limit the scope of this disclosure.

Methods and Materials

1 Reagents and Instruments

Dimethyl sulfoxide (DMSO), 2,6-di-tert-butylated hydroxytoluene (BHT), 1,1-diphenyl-2-picrylhydrazyl (DPPH), isobutylmethylxanthine (IBMX), 3-(4,5-dimethylthiazol-2-yl)-2,5-diphenyltetrazolium bromide (MTT), tannic acid, L-tyrosine, ascorbic acid and diethylene glycol were purchased from Sigma (USA). Rutin was purchased from Acros (USA) and other reagents were the best grade available. Cells were observed using an inverted microscope (CKX41, Olympus, Japan) and cultured in a $CO_2$ incubator (MCO-15AC, Sanyo Electric, Japan).

2. Sample

*Sophora japonica* methanol extract acquired from Korea Plant Extract Bank was used after dissolving in DMSO.

3. Measurement of Antioxidant Activity 3-1. Total Polyphenol Content

Total polyphenol content was colorimetrically quantified according to the Folin-Denis method (Folin and Denis 1912). To 1 mL of appropriately diluted sample was added 1 mL of Folin's reagent. After allowing to settle for 3 minutes and mixing with 1 mL of 10% $Na_2CO_3$, the mixture was allowed to stand at room temperature for 1 hour and absorbance was measured at 760 nm. The calibration curve was prepared using tannic acid.

3-2. Total Flavonoid Content

Total flavonoid content was measured according to an adaptation of the Davis's method (AOAC 1995). To 1 mL of appropriately diluted sample solution were added 10 mL of di(ethylene glycol) and 1 mL of 1 N NaOH. After mixing well and allowing to react in a water bath of 37° C. for 1 hour, absorbance was measured at 420 nm. The calibration curve was prepared using rutin.

3-3. Electron Donating Ability

Electron donating ability was measured according to the Blois' method (Blois 1958). Freeze-dried powder of *Sophora japonica* methanol extract was dissolved in DMSO at concentrations of 100, 500 and 1,000 μg/mL. After taking 1 mL to a test tube and adding 4 mL of $4 \times 10^{-4}$ M DPPH solution, followed by agitating in a water bath of 60° C. for 10 seconds and allowing to stand at room temperature for 20 minutes, absorbance was measured at 525 nm. For the non-extract-treated group, 1 mL of methanol was added instead of the sample. Electron donating ability was calculated from the difference in absorbance relative to the non-treated group. The synthetic antioxidant BHT was used as positive control. Electron donating ability (%) was calculated according to the following equation: Electron donating ability (%)=(1−Absorbance of extract-treated group/Absorbance of non-extract-treated group)×100.

4. In vitro Cell Experiment 4-1. Cell Line and Culturing

Melan-a cells, which are immortalized cells derived from C57BL/6 mouse, were cultured in a 37° C., 10% $CO_2$ incubator using RPMI-1640 medium containing 10% fetal bovine serum (FBS) 1% penicillin/streptomycin (P/S) and 200 nM 12-O-tetradecanoylphorbol 13-acetate (TPA).

4-2. MTT Assay

The MTT assay is a typical technique of measuring cell viability. Upon absorption into cells, 3-(4,5-Dimethylthiazol-2-yl)-2,5-diphenyltetrazolium bromide (MTT) is reduced by succinate dehydronase in mitochondria to formazan. Thus, accumulation of this substance in cells is a measure of mitochondrial activity or, in a broader sense, cell activity. Melan-a cells were stabilized in RPMI-1640 medium containing 10% FBS, 1% P/S and 200 nM TPA in a 10% $CO_2$ incubator at 37° C. for 48 hours before carrying out experiment. The Melan-a cells were seeded on a 96 well plate ($0.5 \times 10^4$ cells/well) and cultured in a 10% $CO_2$ incubator at 37° C. for 24 hours. Then, after adding 200 μL of *Sophora japonica* methanol extract diluted to various concentrations (25, 50, 100 and 200 μg/mL), the cells were further cultured in a 10% $CO_2$ incubator at 37° C. for 48 hours. After centrifuging the plate at 1,000 rpm for 10 minutes and washing once with PBS, 200 μL of medium containing 0.5 mg/mL MTT was added and the cells were further cultured in a 10% $CO_2$ incubator at 37° C. for 3 hours. After centrifuging the plate at 1,000 rpm for 10 minutes so that the cells settled down at the bottom, the medium was discarded and 200 μL of DMSO was added. After dissolving the cells in a plate shaker for 15 minutes, absorbance was measured at 540 nm using an ELISA reader. Cell proliferation was calculated according to the following equation: Cell proliferation (%)=(Absorbance of extract-treated group/Absorbance of non-extract-treated group)×100.

4-3. Melanin Producing Ability

Melan-a cells were stabilized in RPMI-1640 medium containing 10% FBS, 1% P/S and 200 nM TPA in a 10% $CO_2$ incubator at 37° C. for 72 hours before carrying out experiment. The Melan-a cells were seeded on a 96 well plate ($2 \times 10^4$ cells/well) and cultured in a 10% $CO_2$ incubator at 37° C. for 24 hours. Then, after adding 500 μL of *Sophora japonica* methanol extract diluted to various concentrations (6.25, 12.5, 25 and 50 μg/mL), the cells were cultured in a 10% $CO_2$ incubator at 37° C. for 72 hours. Then, after treating again with the *Sophora japonica* methanol extract, the cells were further cultured for 72 hours. After dissolving melanin with 1 N NaOH solution, absorbance was measured at 490 nm. IBMX was used as positive control. Melanin concentration was calculated according to the following equation: Melanin concentration (%)=(Absorbance of extract-treated group/Absorbance of non-extract-treated group)×100.

4-4. Observation of Cell Morphology

In order to observe any change in cell morphology, the cells were observed using an inverted microscope after replacing the medium with fresh one.

4-5. Measurement of intracellular tyrosinase activity

Melan-a cells were stabilized in RPMI-1640 medium containing 10% FBS, 1% P/S and 200 nM TPA in a 10% $CO_2$ incubator at 37° C. for 72 hours before carrying out experiment. The Melan-a cells were seeded on a round 60 φ cell culture dish ($4 \times 10^5$ cells/well) and cultured in a 10% $CO_2$ incubator at 37° C. for 24 hours. Then, after adding 5 mL of *Sophora japonica* methanol extract diluted to various concentrations (6.25, 12.5, 25 and 50 μg/mL), the cells were cultured in a 10% $CO_2$ incubator at 37° C. for 72 hours. Then, after removing the medium and washing with PBS, the cells were lysed by adding 200 μL of 1% Triton X-100 solution. The lysed cells were transferred to an e-tube and vortexed on ice with 10-minute intervals. After about 1 hour, centrifuge was carried out at 4° C. and 14,000 rpm for 20 minutes. The supernatant was subjected to tyrosinase activity measurement. Absorbance was measured using a protein assay solution (Bio-Rad, USA), and the protein quantity was calculated. Cell extract containing 40 μg of protein was mixed with the test substance to a total volume of 100 μL. After adding 100 μL of L-DOPA, followed by incubation in a 10% $CO_2$ incubator at 37° C. for 60 minutes, absorbance was measured at 490 nm. IBMX was used as positive control.

4-6. Activity of Cell-extracted Tyrosinase

Melan-a cells were stabilized in RPMI-1640 medium containing 10% FBS, 1% P/S and 200 nM TPA in a 10% $CO_2$ incubator at 37° C. for 72 hours before carrying out experiment. The Melan-a cells were seeded on a round 60 φ cell culture dish ($4 \times 10^5$ cells/well) and cultured in a 10% $CO_2$ incubator at 37° C. for 72 hours. After washing with PBS and lysing by adding 200 μL of 1% Triton X-100, the lysed cells were transferred to an e-tube and vortexed on ice with 10-minute intervals. After about 1 hour, centrifuge was carried out at 4° C. and 14,000 rpm for 20 minutes. 50 μL of the supernatant was mixed with 49 μL of 0.1 M phosphate buffer (pH 6.8) and 1 μL of Sophora japonica methanol extract at various concentrations (6.25, 12.5, 25 and 50 μg/mL). After allowing to stand for 1 hour, 100 μL of L-DOPA was added. Then, after incubation in a 10% $CO_2$ incubator at 37° C. for 60 minutes, absorbance was measured at 490 nm. IBMX was used as positive control.

4-7. RT-PCR

Total RNA was prepared using Trizol reagent (Invitrogen, Caylsbad, Calif.) according to the manufacturer's instructions. 5 μg of total RNA was subjected to reverse transcription with 8 μL of M-MLV RT 5× buffer, 3 μL of 10 mM dNTPs, 0.45 μL of 10,000 U RNase inhibitor, 0.3 μL of 50,000 U M-MLV reverse transcriptase (Promega, Madison, USA) and 1.5 μL of 50 pmol/μL oligo dT (Bioneer, Daejeon, Korea). Single-stranded cDNA was amplified by PCR in a reaction solution containing 4 μL of 5× green Go Taq flexi buffer, 0.4 μL of 10 mM dNTPs, 0.1 μL of 500 U Taq polymerase, 1.2 μL of 25 mM $MgCl_2$ (Promega, Madison, USA) and 0.4 μL of 20 pmol/μL sense and antisense primers of tyrosinase, TRP-1, TRP-2, MITF-M or β-actin. Sequences of the primers used in the PCR and expected PCR product size are shown in Table 1. β-actin was used as internal standard (51° C., 30 cycles), and test substances were tyrosinase (56° C., 28 cycles), TRP-1 (56° C., 28 cycles), TRP-2 (64° C., 28 cycles) and MITF-M (54° C., 30 cycles). The PCR product was analyzed by electrophoresis on 1.2% agarose gel.

5. Statistical Analysis

Identity was analyzed by one-way analysis of variance (ANOVA) using SPSS (version 17.0). Post-hoc comparison between the groups was performed by Duncan's multiple range test. The statistical significance was tested at α=0.001., α=0.01 and α=0.05.

Experimental Result

1. In vitro Antioxidant Activity 1-1. Total Polyphenol Content

Total polyphenol content of the Sophora japonica extract was 38.9 mg/g (see FIG. 1).

1-2. Total Flavonoid Content

Total flavonoid content of the Sophora japonica extract was 65.2 mg/g (see FIG. 1).

1-3. Electron Donating Ability

Figure 2:
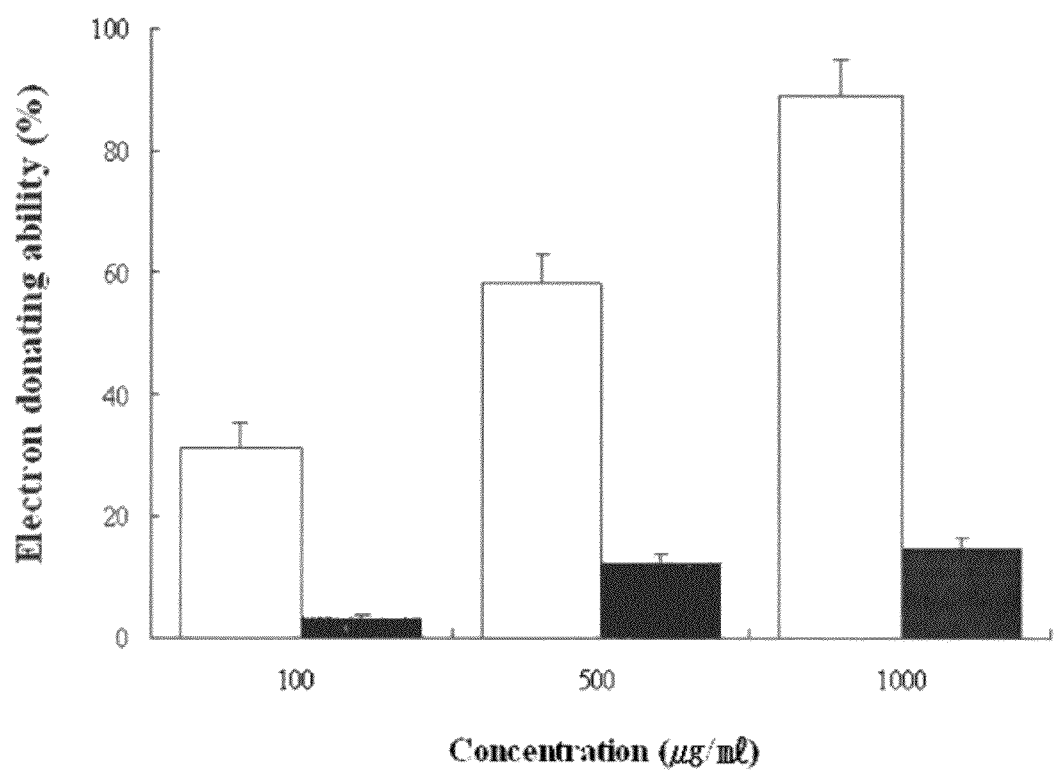
FIG. 2 shows a result of measuring the electron donating ability of *Sophora japonica* methanol extract [Values are mean±SD of 3 measurements. □: BHT (dibutylated hydroxytoluene), ■: SJME]

Both the positive control BHT and the Sophora japonica extract showed positive (+) concentration-dependent relationship. Electron donating ability at 1,000 μg/mL was 85.0% and 14.6%, respectively (see FIG. 2).

2. In vitro Cell Experiment 2-1. MTT Assay

Figure 3:
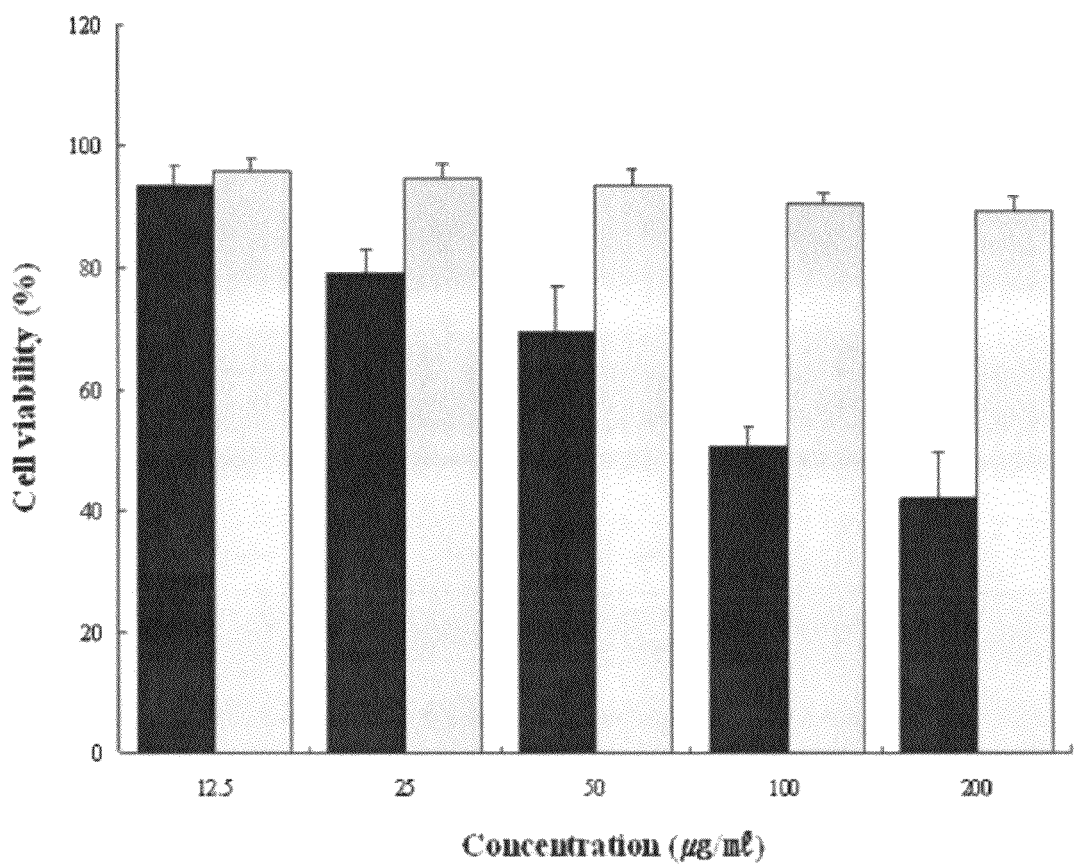
FIG. 3 shows a result of measuring the viability of Melan-a cells treated with *Sophora japonica* methanol extract at various concentrations [Values are mean±SD of 3 measurements. □: IBMX (3-isobutyl-1-methylxanthine), ■: SJME]

The Sophora japonica extract showed cell viability of the Melan-a cells of at least 89% for all of 25, 50, 100 and 200 μg/mL, suggesting that the toxicity is insignificant. The maximum permissible level (MPL) was above 200 μg/mL, whereas that of IBMX was 12.5 μg/mL (see FIG. 3).

2-2. Melanin Producing Ability

Figure 4:
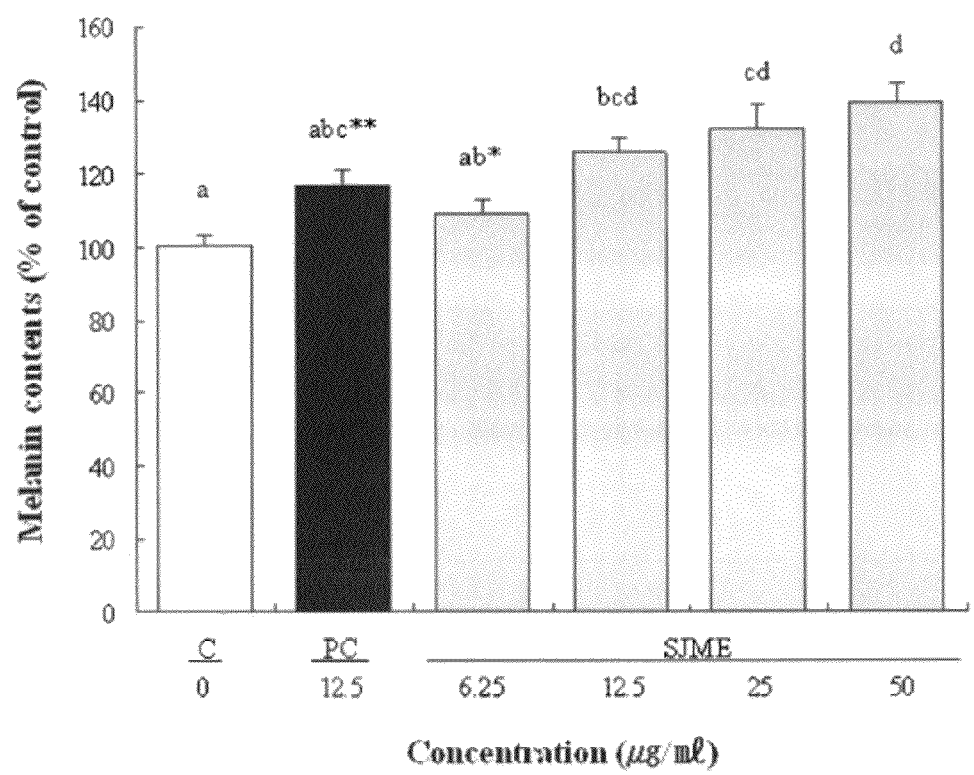
FIG. 4 shows a result of measuring the melanin production promoting effect of *Sophora japonica* methanol extract in Melan-a cells [Values are mean±SD of 3 measurements. C: control, PC (positive control): IBMX, SJME: *Sophora japonica* methanol extract. Values with different superscripts are significantly different ($p<0.001$) by ANOVA and Duncan's multiple range test. Comparison with the control group by ANOVA and Duncan's multiple range test: *$p<0.05$, **$p<0.01$]

When compared with the control, the positive control IBMX showed the most melanin content of 16.7% (p<0.01) at 12.5 μg/mL, and the Sophora japonica extract showed higher melanin content of 9.4% (p<0.05), 25.5% (p<0.001), 32.5% (p<0.001) and 39.6% (p<0.001) at 6.25, 12.5, 25 and 50 μg/mL, respectively (see FIG. 4).

2-3. Observation of Cell Morphology

Figure 5:
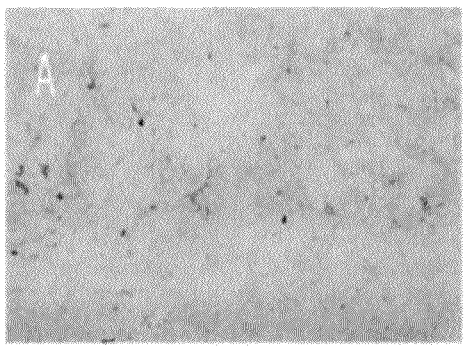
FIG. 5 shows a morphological observation result of Melan-a cells treated with *Sophora japonica* methanol extract [panel A: non-treated group, panel B: SJME (6.25 μg/mL), panel C: SJME (12.5 μg/mL), panel D: SJME (25 μg/mL), panel E: SJME (50 μg/mL), panel F: IBMX (12.5 μg/mL)
Figure 5:
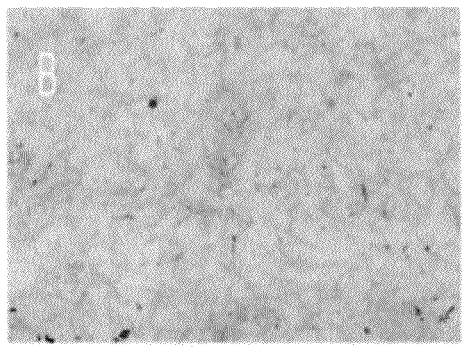
Figure 5:
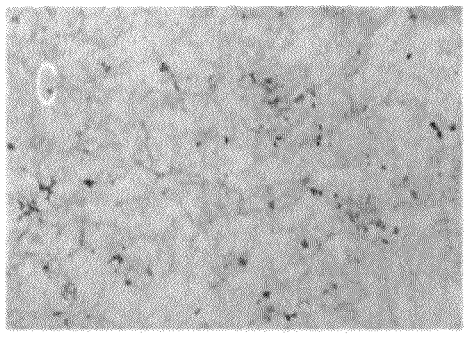
Figure 5:
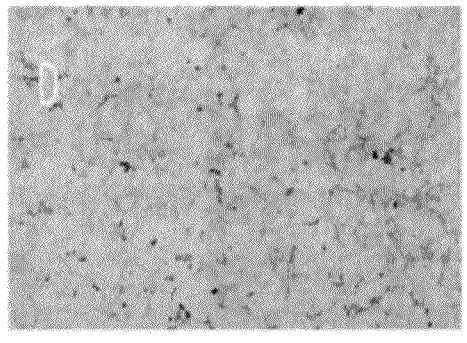
Figure 5:
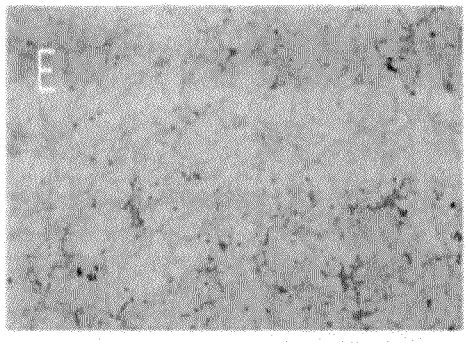
Figure 5:
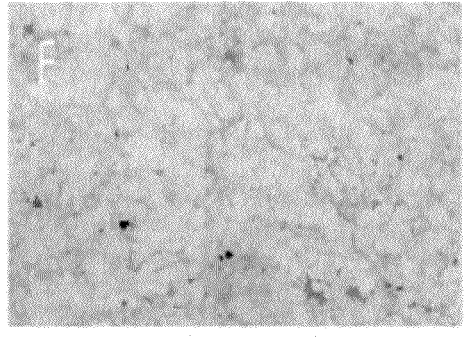

As a result of the morphological observation of the Melan-a cells treated with the sample at various concentrations, the Sophora japonica methanol extract-treated groups showed concentration-dependent increase in development of dendrites and melanin pigmentation. The degree of development of dendrites and melanin pigmentation was higher compared to the control and the positive control IBMX (see FIG. 5).

TABLE 1

| Items | Primers | | Expected size(bp)[1] |
|---|---|---|---|
| Tyrosinase[2] | F3) (5'→3') | CAT TTT TGA TTT GAG TGT CT | 1192 |
| | R4) (5'→3') | TGT GGTAGT CGT CTT TGT CC | |
| TRP-1[5] | F (5'→3') | GCT GCAGGA GCC TTC TTT CTC | 268 |
| | R (5'→3') | AAG ACGCTG CAC TGC TGG TCT | |
| TRP-2[6] | F (5'→3') | GGA TGACCG TGA GCA ATG GCC | 1044 |
| | R (5'→3') | CGG TTGTGA CCA ATG GGT GCC | |
| MITF-M[7] | F (5'→3') | TAC AGA AAG TAG AGG GAG GAG GAC TAAG | 326 |
| | R (5'→3') | CAC AGT TGG AGT TAA GAG TGA GCA TAG CC | |
| β-Actin[8] | F (5'→3') | ACCGTG AAA AGA TGA CCC AG | 528 |
| | R (5'→3') | TACGGA TGT CAA CGT CAC AC | |

Figure 6:
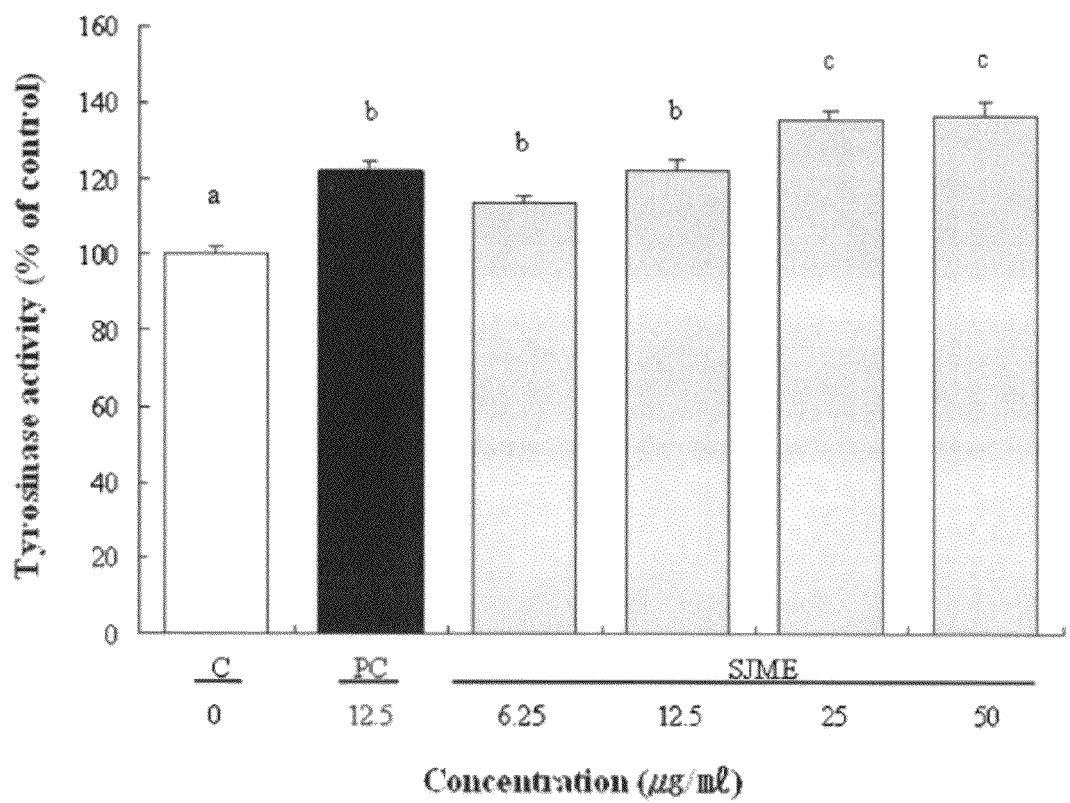
FIG. 6 shows a result of measuring the intracellular tyrosinase activity promoting effect of *Sophora japonica* methanol extract in Melan-a cells [Values are mean±SD of 3 measurements. C: control, PC: IBMX, SJME: *Sophora japonica* methanol extract. Values with different superscripts are significantly different ($p<0.001$) by ANOVA and Duncan's multiple range test]

[1] bp: basepair
[2] Tyrosinase: monophenol monooxygenase
[3] F: forward
[4] R: reverse
[5] TRP-1: tyrosinase-related protein-1
[6] TRP-2: tyrosinase-related protein-2
[7] MITF-M: microphthalmia-associated transcription factor-M
[8] β-Actin: glyceraldehyde-3-phosphate dehydrogenase 2-4. Activity of Intracellular Tyrosinase When compared with the control, the *Sophora japonica* extract-treated groups showed higher activity of 13.6% ($p<0.001$), 21.9% ($p<0.001$), 35.5% ($p<0.001$) and 36.3% ($p<0.001$) at 6.25, 12.5, 25 and 50 μg/mL, respectively, and the positive control IBMX showed higher activity of 22.2% ($p<0.001$) at 12.5 μg/mL (see FIG. 6).

2-5. Activity of Cell-extracted Tyrosinase

Figure 7:
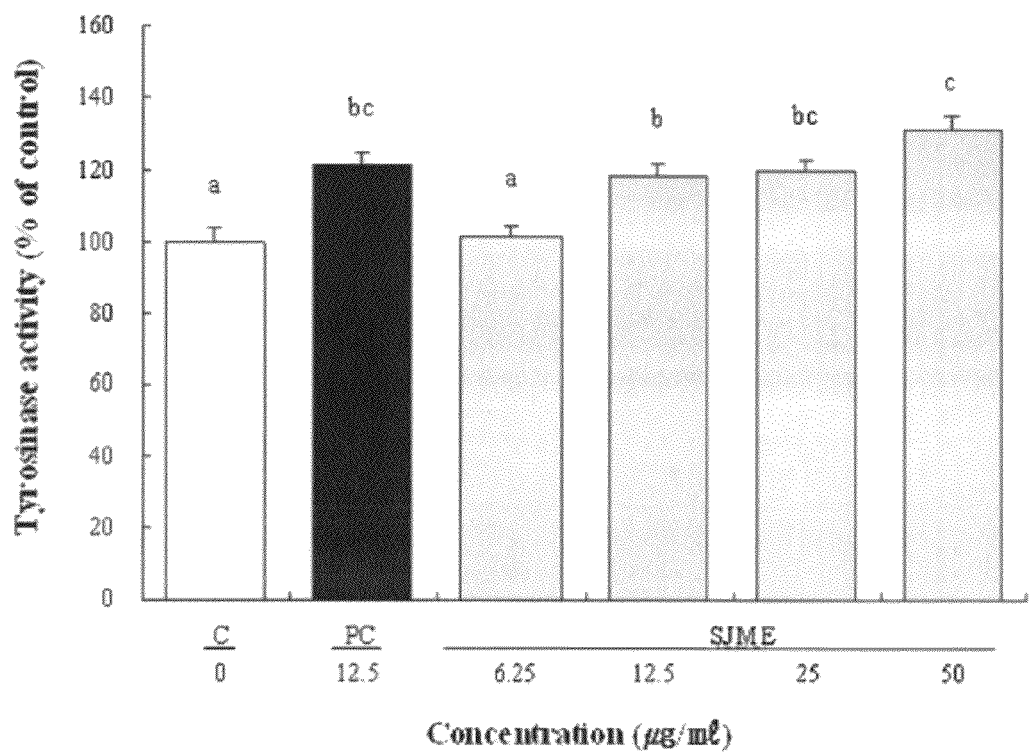
FIG. 7 shows a result of measuring the tyrosinase activity promoting effect of *Sophora japonica* methanol extract in extract of Melan-a cells (Values are mean±SD of 3 measurements. C: control, PC: IBMX, SJME: *Sophora japonica* methanol extract. Values with different superscripts are significantly different ($p<0.001$) by ANOVA and Duncan's multiple range test)

When compared with the control, the *Sophora japonica* extract-treated groups showed higher activity of 1.6%, 17.9% ($p<0.001$), 20.1% ($p<0.001$) and 31.3% ($p<0.001$) at 6.25, 12.5, 25 and 50 μg/mL, respectively, and the positive control IBMX showed higher activity of 21.2% ($p<0.001$) at 12.5 μg/mL (see FIG. 7).

2-6. Effect of SJME on Expression of Tyrosinase mRNA

Figure 8:
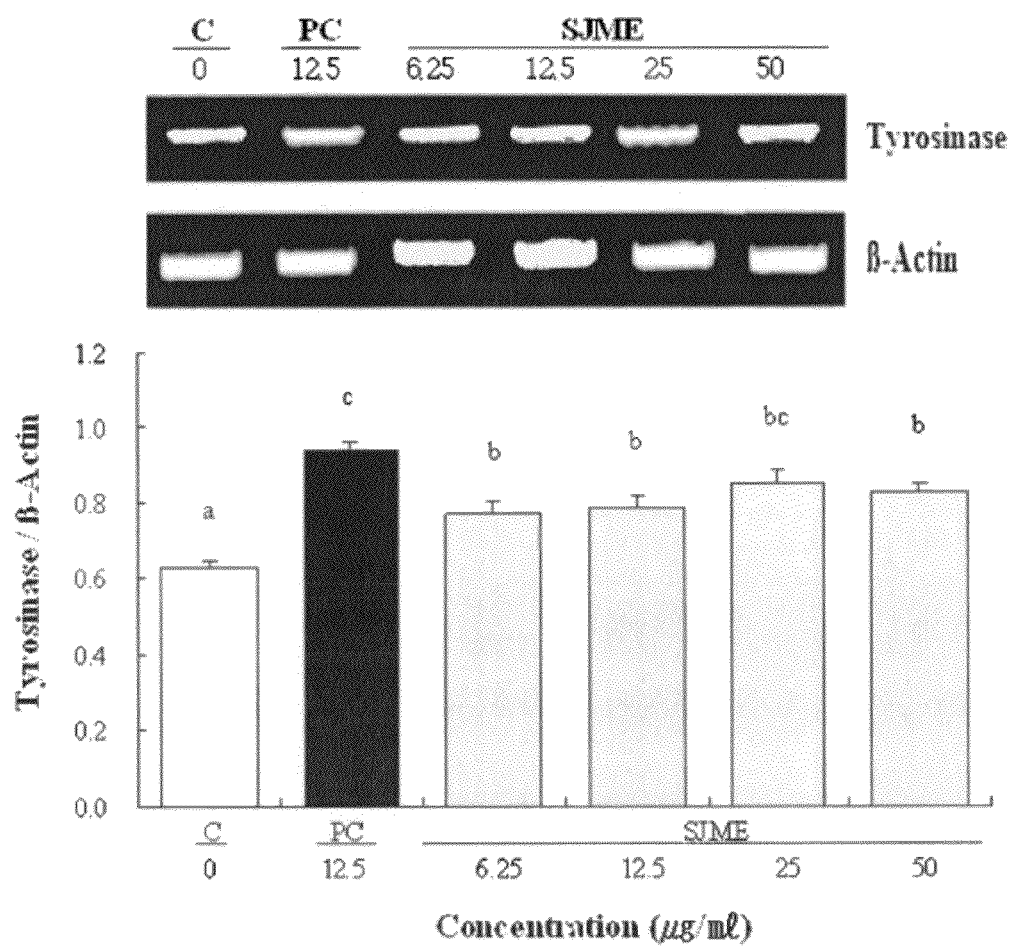
FIG. 8 shows a result of measuring the effect of *Sophora japonica* methanol extract on expression of tyrosinase mRNA in Melan-a cells [Values are mean±SD of 3 measurements. C: control, PC: IBMX, SJME: *Sophora japonica* methanol extract. Values with different superscripts are significantly different ($p<0.001$) by ANOVA and Duncan's multiple range test]

When compared with the control, the *Sophora japonica* extract-treated groups showed higher expression of 14% ($p<0.001$), 16% ($p<0.001$), 22% ($p<0.001$) and 20% ($p<0.001$) at 6.25, 12.5, 25 and 50 μg/mL, respectively, and the positive control IBMX showed higher expression of 0.31% ($p<0.001$) at 12.5 μg/mL (see FIG. 8).

2-7. Effect of SJME on Expression of TRP-1 mRNA

Figure 9:
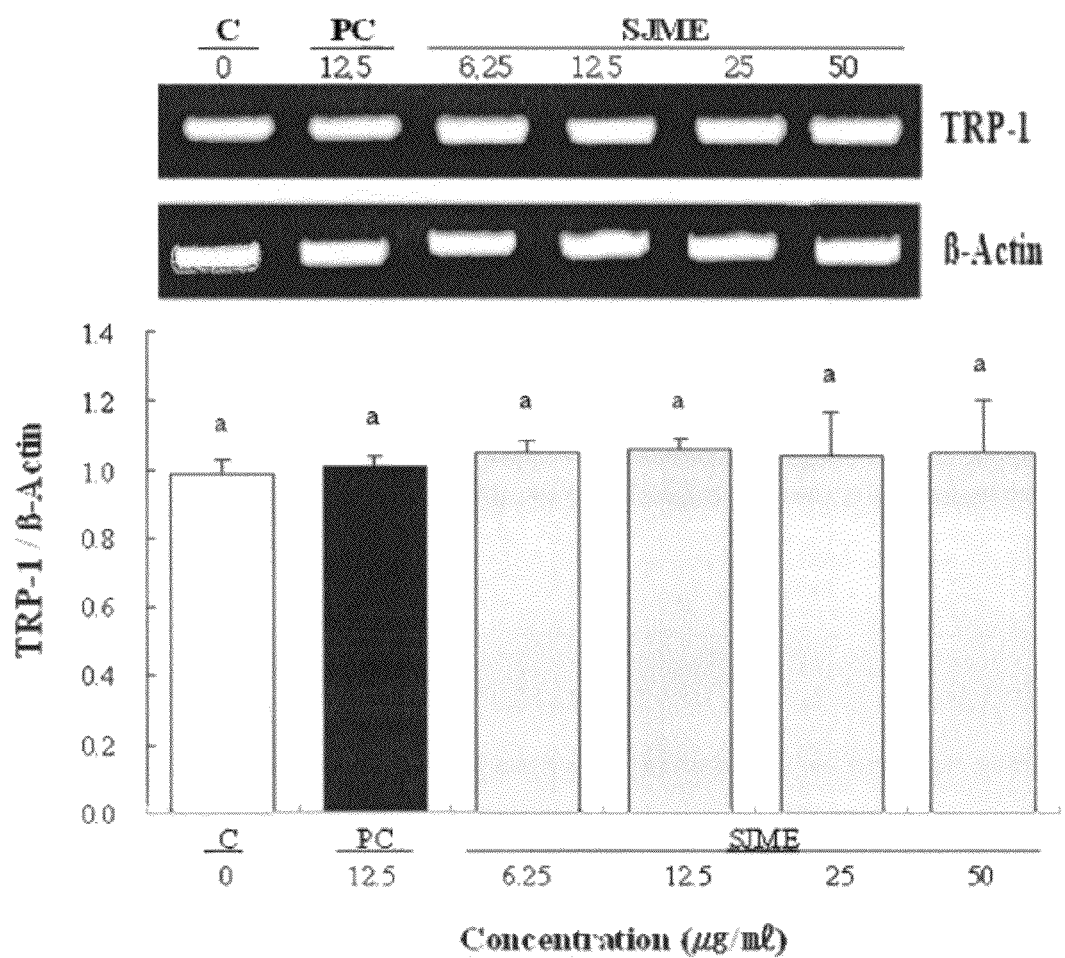
FIG. 9 shows a result of measuring the effect of *Sophora japonica* methanol extract on expression of TRP-1 mRNA in Melan-a cells [Values are mean±SD of 3 measurements. C: control, PC: IBMX, SJME: *Sophora japonica* methanol extract. Values with different superscripts are significantly different ($p<0.001$) by ANOVA and Duncan's multiple range test]

When compared with the control, the *Sophora japonica* extract-treated groups showed higher expression of 6%, 7%, 5% and 6% at 6.25, 12.5, 25 and 50 μg/mL, respectively, and the positive control IBMX showed higher expression of 2% at 12.5 μg/mL, although not significant (see FIG. 9).

2-8. Effect of SJME on Expression of TRP-2 mRNA

Figure 10:
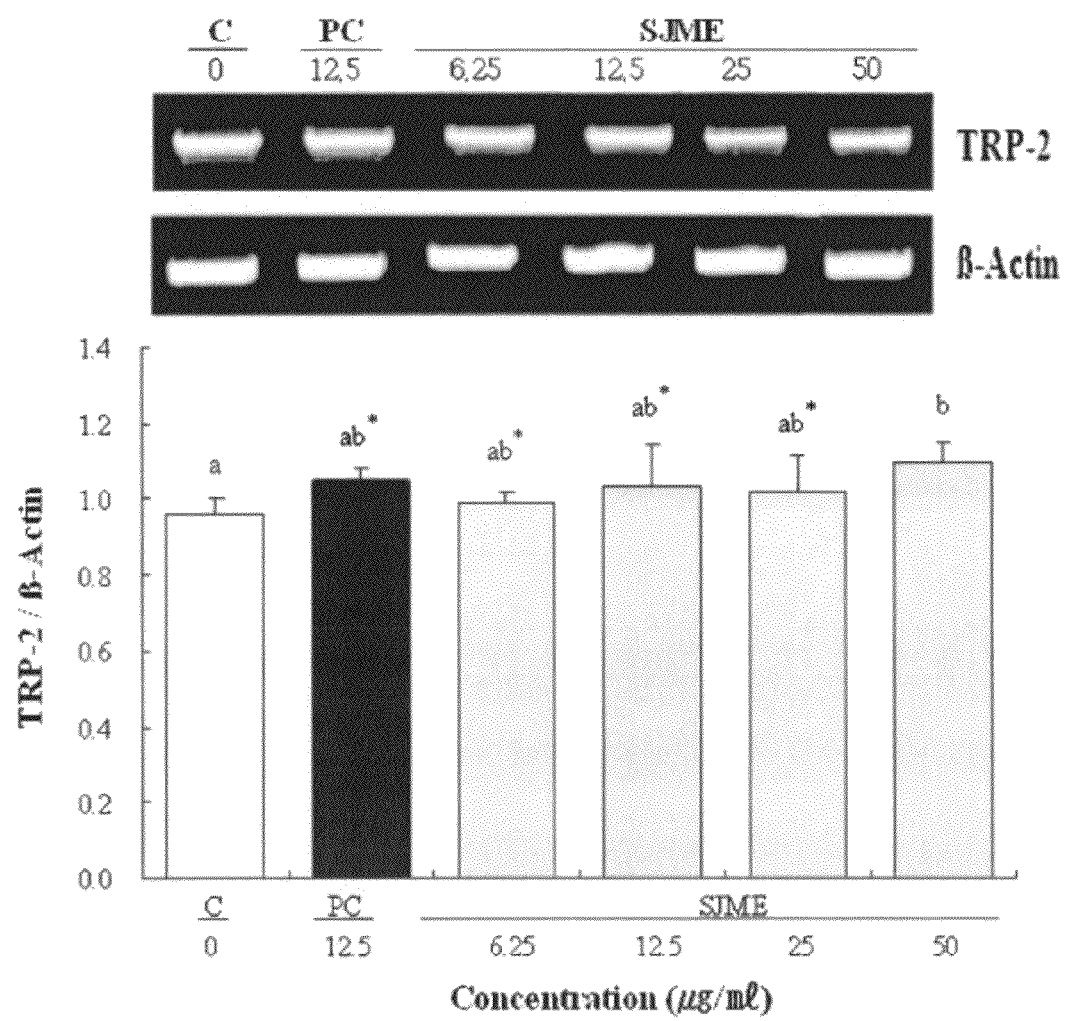
FIG. 10 shows a result of measuring the effect of *Sophora japonica* methanol extract on expression of TRP-2 mRNA in Melan-a cells [Values are mean±SD of 3 measurements. C: control, PC: IBMX, SJME: *Sophora japonica* methanol extract. Values with different superscripts are significantly different ($p<0.001$) by ANOVA and Duncan's multiple range test. Comparison with the control group by ANOVA and Duncan's multiple range test: *$p<0.05$]

When compared with the control, the *Sophora japonica* extract-treated groups showed higher expression of 3% ($p<0.05$), 14% ($p<0.05$), 6% ($p<0.05$) and 7% ($p<0.05$) at 6.25, 12.5, 25 and 50 μg/mL, respectively, and the positive control IBMX showed higher expression of 9% ($p<0.05$) at 12.5 μg/mL (see FIG. 10).

2-9. Effect of SJME on Expression of MITF-M mRNA

Figure 11:
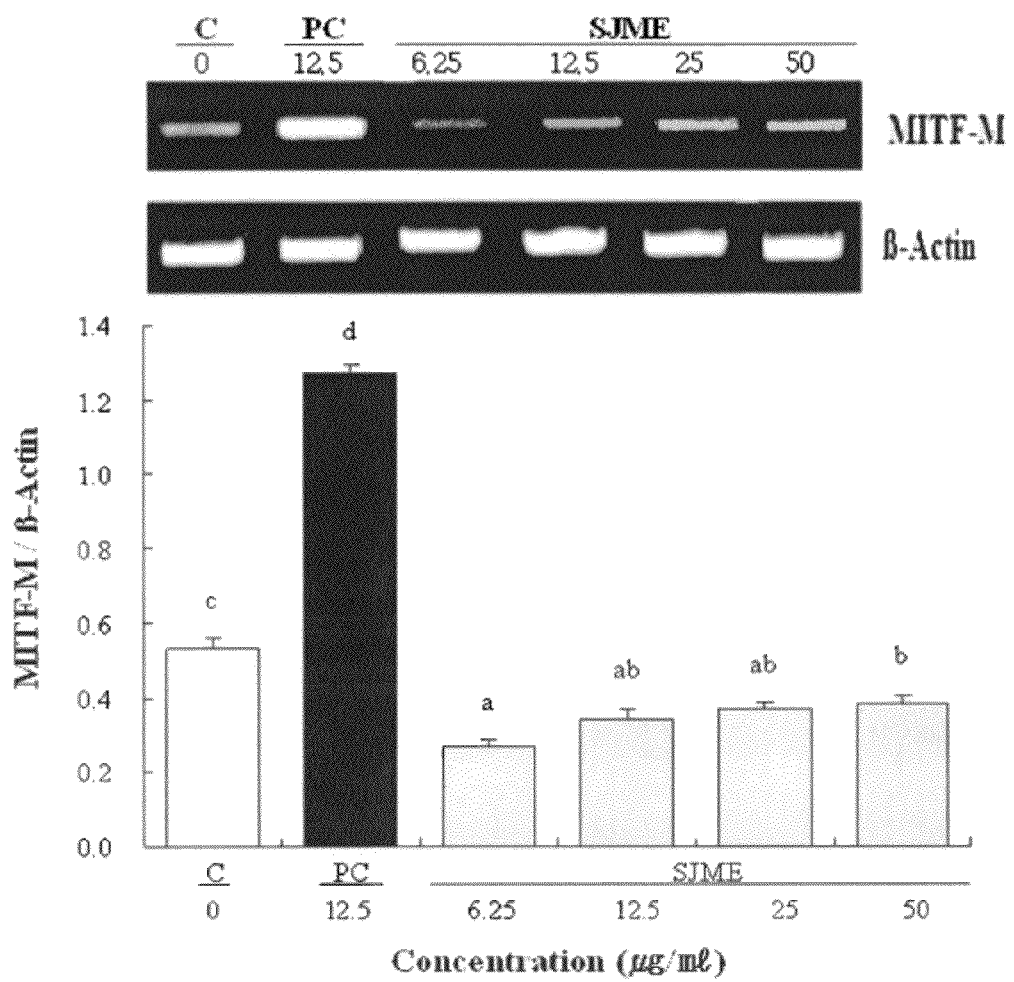
FIG. 11 shows a result of measuring the effect of *Sophora japonica* methanol extract on expression of MITF-M mRNA in Melan-a cells [Values are mean±SD of 3 measurements. C: control, PC: IBMX, SJME: *Sophora japonica* methanol extract. Values with different superscripts are significantly different ($p<0.001$) by ANOVA and Duncan's multiple range test. Comparison with the control group by ANOVA and Duncan's multiple range test: *$p<0.05$].

When compared with the control, all the *Sophora japonica* extract-treated groups showed lower expression, whereas the positive control IBMX showed higher expression of 74% ($p<0.001$) at 12.5 μg/mL (see FIG. 11).

As described above, the present disclosure provides a composition for treating, preventing or improving vitiligo or canities comprising *Sophora japonica* extract as an active ingredient. The *Sophora japonica* extract enhances melanin synthesis by increasing the activity of tyrosinase which is critical in intracellular melanin synthesis and promoting the expression of tyrosinase and TRP-2 mRNA. Furthermore, since the *Sophora japonica* extract is a natural substance with little cytotoxicity, it may be developed into a therapeutic agent for vitiligo and canities caused by depigmentation in skin and hair.

While the present disclosure has been described with respect to the specific embodiments, it will be apparent to those skilled in the art that various changes and modifications may be made without departing from the spirit and scope of the disclosure as defined in the following claims.

References

Amae, S., N. Fuse, K. Yasumoto, S. Sato, I. Yajima, H. Yamamoto, T. Udono, Y. K. Durlu, M. Tamai, K. Takahashi, and S. Shibahara. 1998. Identification of a novel isoform of microphthalmia-associated transcription factor that is enriched in retinal pigment epithelium. *Biochemical and Biophysical Research Communications* 247: 710-715.

A.O.A.C. 1995. Association of Official Analytical Chemists. Official methods of analysis (12th). Washington D.C.: A.O.A.C.

Beecher, G. R. 2003. Overview of dietary flavonoids: nomenclature, occurrence and intake. *Journal of Nutritional Biochemistry* 133: 3248-3254.

Blois, M. S. 1958. Antioxidant determination by the use of a stable free radical. *Nature* 181: 1199-1200.

Boude, A. M. 2007. Evolution and current status of research in phenolic compounds. *Phytochemistry* 68: 2722-2735.

Chung, S. W., Y. M. Ha, Y. J. Kim, S. Song, H. Lee, H. Suh, and H. Y. Chung. 2009. Inhibitory effects of 6-(3-hydroxyphenyl)-2-naphthol on tyrosinase activity and melanin synthesis. *Archives of Pharmacal Research* 2: 289-294.

David, A. B. 2001. Skin pigmentation enhancers. *Journal of Photochemistry and Photobiology B: Biology* 63: 148-161.

Di, C. G., M. Mascolo, A. A. Izzo, and F. Capasso. 1999. Flavonoids: old and new aspects of a class of natural therapeutic drugs. *Life Science* 65: 337-353.

Eklund, P. C., O. K. Langvik, J. P. Warna, T. O, Salmi, S. M. Willfor, and R. E. Sjoholm. 2005. Chemical studies on antioxidant mechanisms and free radical scavenging properties of lignans. *Organic and Bimolecular Chemistry* 21: 3336-3347.

Fan, L., Y. Dongsheng, X. Zhou, Hu. D. N, and Q. Jia. 2007. Expression of melanin-related genes in cultured adult human retinal pigment epithelium and uveal melanoma cells. *Molecular Vision* 13: 2066-2072.

Folin, O., and W. Denis. 1912. On phosphotungstic-phosphomolybdic compounds as color reagents. *Journal of Biochemistry and Chemistry* 12: 239-249.

Fuse, N., K. Yasumoto, K. Takeda, S. Amae, M. Yoshizawa, T. Udono, K. Takahashi, M. Tamai, Y. Tomita, M. Tachibana, and S. Shibahara. 1999. Molecular cloning of cDNA encoding a novel microphthalmia-associated transcription factor isoform with a distinct amino-terminus. *Journal of Biochemistry* 126: 1043-1051.

Grupp, C., H. John, U. Hemprich, A. Singer, U. Munzel, and G. A. Muller. 2001. Identification of nucleated cells in urine using lectin staining. *American Journal of Kidney Diseases* 37: 84-93.

Hwang, S. H., S. Y. Choi, J. H. Lee, S, N. Kim, J. K. In, S. K. Ha, E. J. Lee, T. Y. Kim, S. Y. Kim, S. Choi, and S. H. Kim. 2010. Identification of a potent and noncytotoxic inhibitor of melanin production. *Bioorganic & Medicinal Chemistry* 18: 5602-5609.

Helen, K. E., G. G. Nikos, J. G. David, and P. W. Anthony. 2007. Autoantibody responses to melanocytes in the depigmenting skin disease vitiligo. *Autoimmunity Reviews* 6: 138-142.

Hershey, C. L., and D. E. Fisher. 2005. Genomic analysis of the microphthalmia locus and identification if MITF-J/Mitf-J isoform. *Gene* 347: 73-82.

Hoganson, G. E., F. Ledwitz-Rigby, R. L. Davidson, B. B. Fuller, C. D. Smith, R. Radi, W. H. Koppenol, and J. S. Beckman. 1994. On the Regulation of tyrosinase mRNA levels in mouse melanoma cell pH-dependent yield of hydroxyl radical products from peroxyclones by melanocyte-stimulating hormone and cyclic AMP, nitrite. *Free Radical Biology & Medicine* 16: 331-338.

Huang, Y. H., T. H. Lee, K. J. Chan, F. L. Hsu, Y. C. Wu, and M. H. Lee. 2008. Anemonin is a natural bioactive compound that can regulate tyrosinase-related proteins and mRNA in human melanocytes. *Journal of Dermatological Science* 49: 115-123.

Huber, W. E., E. R. Price, H. R. Widlund, J. Du, I. J. Davis, M. Wegner, and D. E. Fisher. 2003. A tissue-restricted cAMP transcriptional response: SOX10 modulates a melanocyte-stimulating hormone triggered expression of microphthalmia-associated transcription factor in melanocytes. *Journal of Biological Chemistry* 278: 45224-45230.

Jin, J., Z. Li, and F. Zhang. 2006. Scavenging function of mulberry vinegar extractives for 1,1-diphenyl-2-picrylhydrazyl (DPPH). *Journal of Northwest Sci-Tech University of Agriculture and Forestry* 34: 135-137.

Kent. G., and MSK. Al' Abadie. 1996. Psychologic effects of vitiligo: a critical incident analysis. *Journal of American Academy of Dermatology* 35: 895-898.

Kiken, D. A., and D. E. Cohen. 2002. Contact dermatitis to botanical extracts. *American Journal of Contact Dermatitis* 13: 148-152.

Kim, H. J., S. H. Seo, B. G. Lee, and Y. S. Lee. 2005. Identification of tyrosinase inhibitors from *Glycyrrhiza uralensis*. *Planta Medica* 71: 785-787.

Kim, Y. J., and H. Uyama. 2005. Tyrosinase inhibitors from natural and synthetic sources: structure, inhibition mechanism and perspective for the future. *Molecular and Cellular Biology* 62: 1707-1023.

Koo, J. H., H. T. Kim, H. Y. Yoon, K. B. Kwon, I. W. Choi, S. H. Jung, H. U. Kim, B. H. Park, and J. W. Park. 2008. Effect of xanthohumol on melanogenesis in B16 melanoma cells. *Experimental and Molecular Medicine* 3: 313-319.

Kratchanova, M., P. Denev, M. Ciz, A. Lojek, and A. Mihailov. 2010. Evaluation of antioxidant activity of medicinal plants containing polyphenol compounds. Comparison of two extraction systems. Acta Biochimica Polonica 2: 229-234.

Lee, M. H., Y. P. Lin, F. L. Hsu, G. R. Zhan, and K. Y. Yen. 2006. Bioactive constituents of *Spatholobus suberectus* in regulating tyrosinase-related proteins and mRNA in HEMn cells. *Phytochemistry* 67: 1262-1270.

Levy, C., M. Khaled, and D. E. Fisher. 2006. MITF: master regulator of melanocyte development and melanoma oncogene. *Trends in Molecular Medicine* 12: 406-414.

Loa, Y. H., R. D. Linb, Y. P. Lind, Y. L. Liue, and M. H. Lee. 2009. Active constituents from *Sophora japonica* exhibiting cellular tyrosinase inhibition in human epidermal melanocytes. *Journal of Ethnopharmacology* 124: 625-629.

Lucille. P., J. M. Routaboul 1, V. Cheynier, L. Lepiniec. and I. Debeaujon. 2006. Flavonoid oxidation in plants: from biochemical properties to physiological functions. *Trends in Plant Science Vol.* 12. No. 1.

Ma. L., and F. C. Lou. 2006. The anticancer activity in vitro of constituents from fruits of *Sophora japonica*. *Chinese Journal of Natural Medicines* 4: 151-153.

Manach, C., A. Scalbert, C. Morand, C. Remesy, and L. Jimenez. 2004. Polyphenols: food sources and bioavailability. *American Journal of Clinical Nutrition* 79: 727-747.

Mallick, S., S. K. Singh, C. Sarkar, B. Saha, and R. Bhadra. 2005. Human placental lipid induces melanogenesis by increasing the expression of tyrosinase and its related proteins in vitro. *Pigment Cell Research* 18: 25-33.

Maxine, E., B. A. Whitton, M. Darren. Ashcroft and Urbà González. 2008. Therapeutic interventions for vitiligo. *Journal of the American Academy of Dermatology* 59: 713-717.

Michaela, B., and J. H. Vincent. 2008. Modifying skin pigmentation-approaches through intrinsic biochemistry and exogenous agents. Drug Discovery Today: *Disease Mechanisms* 22: 189-199.

Momtaz, S., N. Lall, and A. Basson. 2008. Inhibitory activities of mushroom tyrosine and DOPA oxidation by plant extracts. *South African Journal of Botany* 74: 577-582.

Moretti. S., A. Spallanzani, L. Amato, G. Hautmann, I. Gallerani, M. Fabiani, and P. Fabbri. 2002. New insights into the pathogenesis of vitiligo: imbalance of epidermal cytokines at sites of lesions. *Pigment Cell Research* 15: 87-92.

Marmol, V., and F. Beermann. 1996. Tyrosinase and related proteins in mammalian pigmentation. *FEBS Letters* 381: 165-168.

Naughton, G. K., M. Eisinger, and J. C. Bystryn. 1983. Antibodies to normal human melanocytes in vitiligo. *Journal of Experimental Medicine* 158: 246-251.

Nordlund, J. J., and A. B. Lerner. 1982. Vitiligo: it is important. *Archives of Dermatology* 118: 5-8.

Oboki, K., E. Morii, T. R. Kataoka, T. Jippo, and Y. Kitamura. 2002. Isoforms of mitranscription factor preferentially expressed in cultured mast cells of mice. *Biochemical and Biophysical Research Communications* 290: 1250-1254.

Ogg, G. S., P. R. Dunbar, P. Romero, J. L. Chen, and V. Cerundolo. 1998. High frequency of skin-homing melanocyte-specific cytotoxic T lymphocytes in autoimmune vitiligo. *Journal of Experimental Medicine* 188: 1203-1208.

Ongenae, K., L. Beelaert, N. V. Geel, and J. M. Naeyaert. 2006. Psychosocial effects of vitiligo. *Journal of the European Academy of Dermatology and Venereology* 20:1-8.

Ongenae, K., N. Van Geel, J. M. Naeyaert. 2003. Evidence for an autoimmune pathogenesis of vitiligo. *Pigment Cell Research* 16: 90-100.

Ozcelik, O., J. H. Lee, and D. B. Min. 2003. Effects of light, oxygen and pH on the Absorbance 330 of 2,2-diphenyl-1-picrylhydrazyl. *Journal of Food Science* 68: 487-490.

Papadopoulos, L., R. Bor, and C. Legg. 1999. Coping with the disfiguring effects of vitiligo: a preliminary investigation into the effects of cognitive-behavioral therapy. *British Journal of Medical Psychology* 72: 385-396.

Paker, L., and A. S. H. Ong. 1998. Biological oxidants and antioxidants: molecular mechanisms and health effects. Champain: AOCS Press.

Parvez, S., M. Kang., H. Chung, C. Cho, M. Hong, M. Shin, and H. Bae. 2006. Survey and mechanism of skin depigmenting and lightening agents. *Phytotherapy Research* 20: 921-934.

Pawelek, J., A. Korner, and A. Bergstrom. 1980. New regulation of melanin biosynthesis and autodestruction of melanoma cells. *Nature* 286: 617-619.

Rajatanavin, N., T. Somsak, T. Wisuttida, and L. Laor. 2003. Narrowband ultraviolet B radiation therapy for recalcitrant vitiligo in Asians. *Journal of American Academy of Dermatology* 3: 473-476.

SCnchez-Moreno, C., J. A. Larrauri, and F. Saura-Calixto. 1998. A procedure to measure the antiradical efficiency of polyphenols. *Journal of Science of Food and Agriculture* 76: 270-276.

Scalbert, A., and G. Williamson. 2000. Dietary intake and bioavailability of polyphenols. *Journal of Nutrition* 130: 2073-2085.

Schallreuter, K. U., J. M. Wood, and J. Berger. 1991. Low catalase levels in the epidermis of patients with vitiligo. *Journal of Investigative Dermatology* 97: 1081-1085.

Shibahara, S., K. Yasumoto, S. Amae, N. Fuse, T. Udono, and K. Takahashi. 1999. Implications of isoform multiplicity of microphthalmia-associated transcription factor in the pathogenesis of auditory-pigmentary syndromes. *Journal of Investigative Dermatology Symposium Proceedings* 4: 101-104.

Stefano, P., and S. Crispian. 2009. Oral health and disease: a review. *Journal of Dentistry* 37: 413-423.

Sturm, R. A., R. D. Teasdale, and N. F. Box. 2001. Human pigmentation genes: identification, structure and consequences of polymorphic variation. *Gene* 277: 49-62.

Takeda, K., K. Yasumoto, N. Kawaguchi, T. Udono, K. Watanabe, H. Saito, K. Takahashi, M. Noda, and S. Shibahara. 2002. Mitf-D, a newly identified isoform, expressed in the retinal pigment epithelium and monocyte-lineage cells affected by Mitf mutations. *Biochimica et Biophysica Acta* 1574: 15-23.

Tiedtke, J., J. Morel, and O. Marks. 2004. Depigmentation factor bioflavonoids—A safe and effective skin lightening based on encapsulated citrus bioflavonoids. *Natural Ingredients* 2004: 12-17.

Tripathi, R. K., V. J. Hearing, K. Urabe, P. Aroca, and R. A. Spritz. 1992. Mutational mapping of the catalytic activities of human tyrosinase. *Journal of Biological Chemistry* 267: 23707-23712.

Udono, T., K. Yasumoto, K. Takeda, S. Amae, K. Watanabe, H. Saito, N. Fuse, M. Tachibana, K. Takahashi, M. Tamai, and S. Shibahara. 2000. Structural organization of the human microphthalmia-associated transcription factor gene containing four alternative promoters. *Biochimica et Biophysica Acta* 491: 205-219.

Vachtenheim, J., and J. Borovansky. 2004. Microphthalmia transcription factor: a specific marker for malignant melanoma. *Prague Medical Report* 105: 318-324.

Vaknin, H., A. B. Akiva, R. Ovadia, A. N. Levi, I. Forer, D. Weiss, and M. O, Shamir. 2005. Active anthocyanin degradation in *Brunfelsia calycina* (yesterday-today-tomorrow) flowers. *Planta* 222: 19-26.

Wang, J. H., Y. L. Wang, and F. C. Lou. J. 2001. Acacia trees the chemical constituents of the seeds. *Journal of China Pharmaceutical University* 32: 471.

Wang, K. H., R. D. Lin, F. L. Hsu, Y. H. Huang, H. C. Chang, C. Y. Huang, and M. H. Lee. 2006. Cosmetic applications of selected traditional Chinese herbal medicines. *Journal of Ethnopharmacology* 106: 353-359.

Wakamatsu, K., R. Kavanagh, A. L. Kadekaro, S. Terzieva, R. A. Sturm, S. Leachman, Z. A. Malek, and S. Ito. 2006. Diversity of pigmentation in cultured human melanocytes is due to differences in the type as well as quantity of melanin. *Pigment Cell Research* 19: 154-162.

Weilbaecher, K. N., G. Motyckova, W. E. Huber, C. M. Takemoto, T. J. Hemesath, Y. Xu, C. L. Hershey, N. R. Dowland, A. G. Wells, and D. E. Fisher. 2001. Linkage of M-CSF signaling to Mitf, TFE3, and the osteoclast defect in Mitf mi/ml mice. *Molecular Cell* 8: 749-758.

Westerhof, W., and M. d'Ischia. 2007. Vitiligo puzzle: the pieces fall in place. *Pigment Cell Research* 20: 345-359.

Yaar, M., C. Wu, H. Y. Park, L. Panova, G. Schutz, and B. A. Gilchrest. 2006. Bone morphogenetic protein-4, a novel modulator of melanogenesis. *Journal of Biological Chemistry* 281: 25307-25314.

Yasumoto, K., K. Yokoyama, K. Takahashi, Y. Tomita, and S. Shibahara. 1997. Functional analysis of microphthalmia-associated transcription factor in pigment cell-specific transcription of the human tyrosinase family genes. *Journal of Biological Chemistry*. 272: 503-509.

Zhao, Z. Z. 2004. An Illustrated Chinese Materia Medica in Hong Kong. School of Chinese Medicine. Hong Kong: Hong Kong Baptist University.

What is claimed is:

1. A method for treating canities comprising topically applying an effective amount of a topical composition consisting essentially of a *Sophoria japonica* extract to one or more areas of the skin of a person in need thereof.

2. The method according to claim 1, wherein said *Sophora japonica* extract is extracted using an extraction solvent selected from the group consisting of water, absolute or aqueous lower alcohol containing 1-4 carbons, acetone, ethyl acetate, butyl acetate, dichloromethane ($CH_2CL_2$), chloroform, hexane and 1,3-butylene glycol.

3. The method according to claim 1, wherein said *Sophora japonica* extract is included at a concentration of 0.001-30 wt % based on the total weight of said topical composition.

4. The method according to claim 1, wherein said topical composition is in the form of an external skin formulation selected from the group consisting of powder, gel, ointment, cream, lotion, liquid and aerosol.

* * * * *

```
SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: PCR forward primer for Tyrosinase

<400> SEQUENCE: 1
catttttgat ttgagtgtct                                              20

<210> SEQ ID NO 2
<211> LENGTH: 20
<212> TYPE: DNA
<213> ORGANISM: Artificial Sequence
<220> FEATURE:
<223> OTHER INFORMATION: PCR reverse primer for Tyrosinase

<400> SEQUENCE: 2
tgtggtagtc gtctttgtcc                                              20

<210> SEQ ID NO 3
<211> LENGTH: 21
<212> TYPE: DNA
<213> ORGANISM: Artificial Sequence
<220> FEATURE:
<223> OTHER INFORMATION: PCR forward primer for TRP-1

<400> SEQUENCE: 3
gctgcaggag ccttctttct c                                            21

<210> SEQ ID NO 4
<211> LENGTH: 21
<212> TYPE: DNA
```

```
<213> ORGANISM: Artificial Sequence
<220> FEATURE:
<223> OTHER INFORMATION: PCR reverse primer for TRP-1

<400> SEQUENCE: 4
aagacgctgc actgctggtc t                                            21

<210> SEQ ID NO 5
<211> LENGTH: 21
<212> TYPE: DNA
<213> ORGANISM: Artificial Sequence
<220> FEATURE:
<223> OTHER INFORMATION: PCR forward primer for TRP-2

<400> SEQUENCE: 5
ggatgaccgt gagcaatggc c                                            21

<210> SEQ ID NO 6
<211> LENGTH: 21
<212> TYPE: DNA
<213> ORGANISM: Artificial Sequence
<220> FEATURE:
<223> OTHER INFORMATION: PCR reverse primer for TRP-2

<400> SEQUENCE: 6
cggttgtgac caatgggtgc c                                            21

<210> SEQ ID NO 7
<211> LENGTH: 28
<212> TYPE: DNA
<213> ORGANISM: Artificial Sequence
<220> FEATURE:
<223> OTHER INFORMATION: PCR forward primer for MITF-M

<400> SEQUENCE: 7
tacagaaagt agagggagga ggactaag                                     28

<210> SEQ ID NO 8
<211> LENGTH: 29
<212> TYPE: DNA
<213> ORGANISM: Artificial Sequence
<220> FEATURE:
<223> OTHER INFORMATION: PCR reverse primer for MITF-M

<400> SEQUENCE: 8
cacagttgga gttaagagtg agcatagcc                                    29

<210> SEQ ID NO 9
<211> LENGTH: 20
<212> TYPE: DNA
<213> ORGANISM: Artificial Sequence
<220> FEATURE:
<223> OTHER INFORMATION: PCR forward primer for beta-Actin

<400> SEQUENCE: 9
accgtgaaaa gatgacccag                                              20

<210> SEQ ID NO 10
<211> LENGTH: 20
<212> TYPE: DNA
<213> ORGANISM: Artificial Sequence
<220> FEATURE:
<223> OTHER INFORMATION: PCR reverse primer for beta-Actin

<400> SEQUENCE: 10
tacggatgtc aacgtcacac                                              20
```